United States Patent [19]

Argabrite et al.

[11] 4,182,192
[45] Jan. 8, 1980

[54] BEAM TYPE HARDNESS TESTER FOR ELASTOMERIC MATERIAL AND METHOD OF TESTING

[75] Inventors: George A. Argabrite, Malibu; William C. Sanford, 22811 Macfarlane Dr., Woodland Hills, both of Calif.

[73] Assignee: William C. Sanford, Woodland Hills, Calif. ; by George A. Angabrite and William C. Sanford

[21] Appl. No.: 946,772

[22] Filed: Sep. 28, 1978

[51] Int. Cl.² .............................................. G01N 3/14
[52] U.S. Cl. ...................................................... 73/818
[58] Field of Search .................................... 73/818, 78

[56] References Cited

U.S. PATENT DOCUMENTS 2,703,492 3/1955 Brissette et al. ....................... 73/818

FOREIGN PATENT DOCUMENTS 730398 1/1943 Fed. Rep. of Germany ............. 73/818
399614 10/1933 United Kingdom ....................... 73/818

Primary Examiner—Gerald Goldberg
Assistant Examiner—Joseph W. Roskos

Attorney, Agent, or Firm—William W. Glenny

[57] ABSTRACT

An apparatus for testing hardness of elastomeric material comprising a pivotally mounted beam assembly for measuring deformation of the material when a calibrated mass is applied thereto. A horizontal anvil member supports the material being tested which is selectively positioned on the anvil member in accordance with a cross-sectional dimension of the material. The calibrated mass or weight is slidably positioned on the beam assembly also in correlation with said dimension. A measuring gauge measures the beam assembly when the test material is gripped between the beam assembly and anvil member, and indicates hardness on a scale correlated to the measured cross-sectional dimension of the material. The gauge and a lateral extension of the beam assembly are magnetically coupled. A method of measuring hardness of elastomeric material including the steps of measuring an unstressed dimension of the material, imposing on the sample material an amount of compressive force determined by the unstressed dimension, and measuring the amount of deformation of the sample.

12 Claims, 7 Drawing Figures

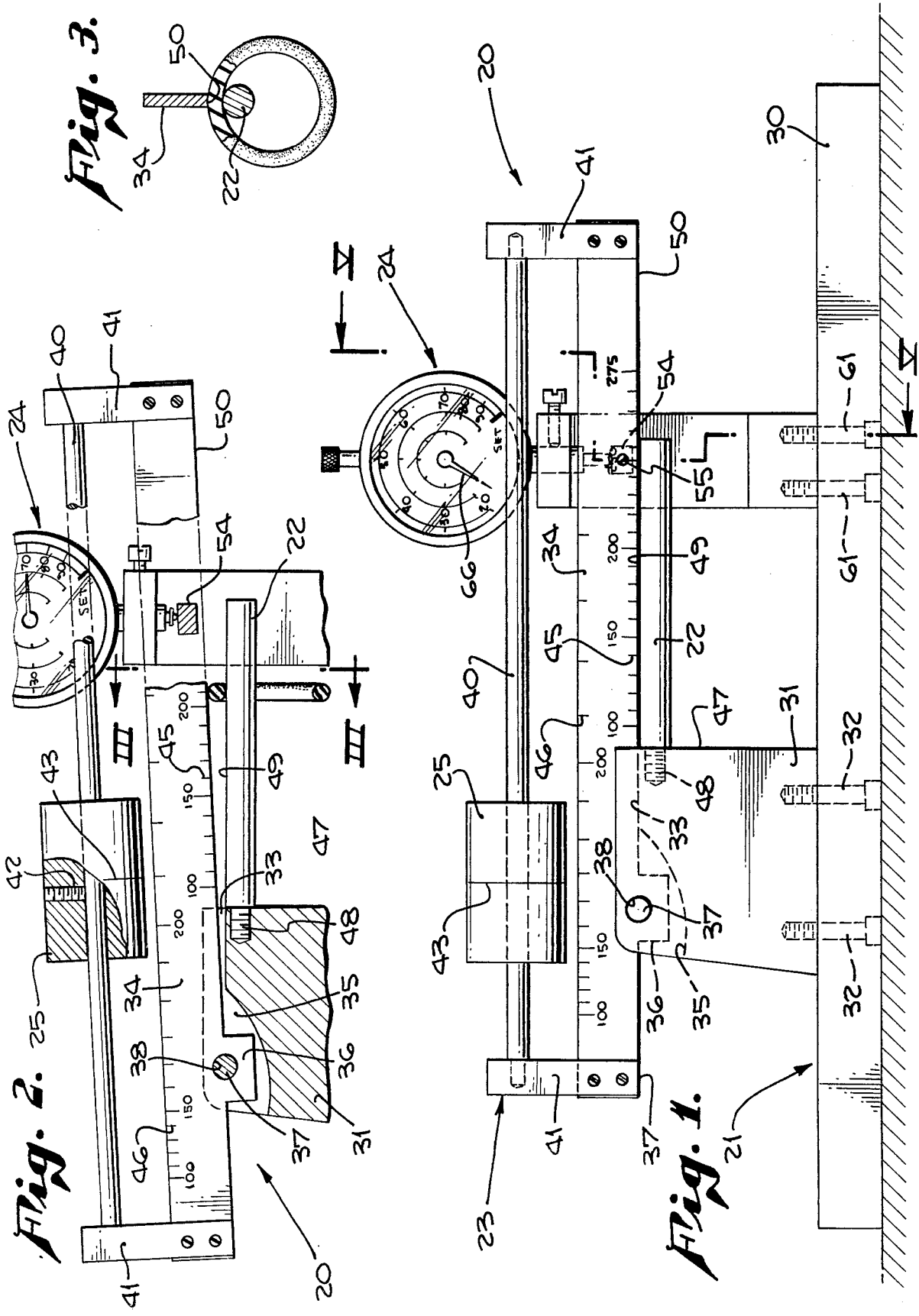

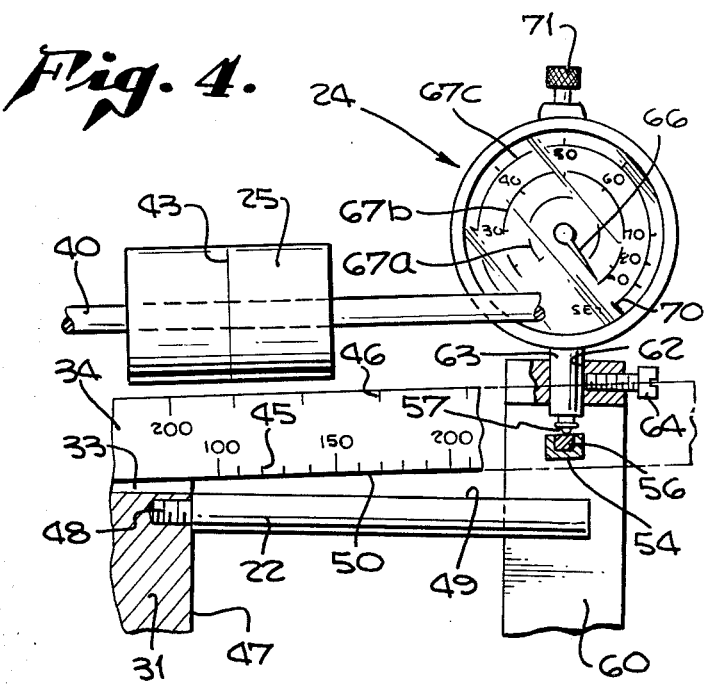
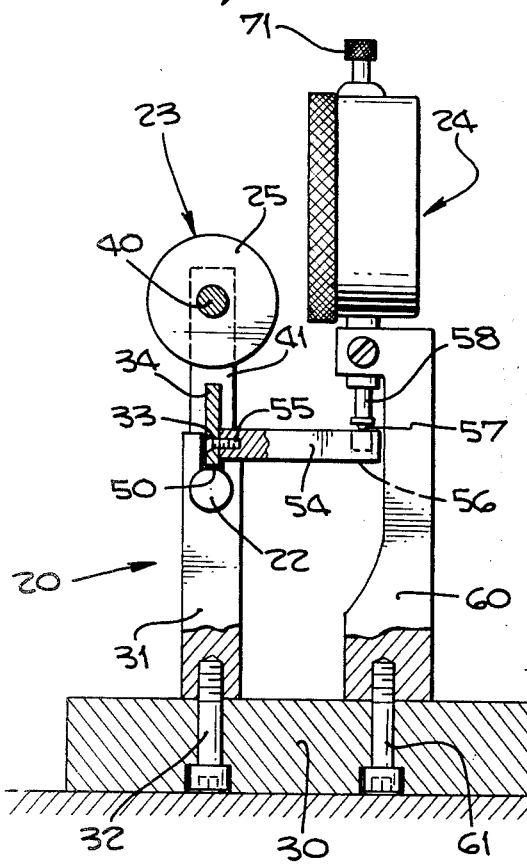
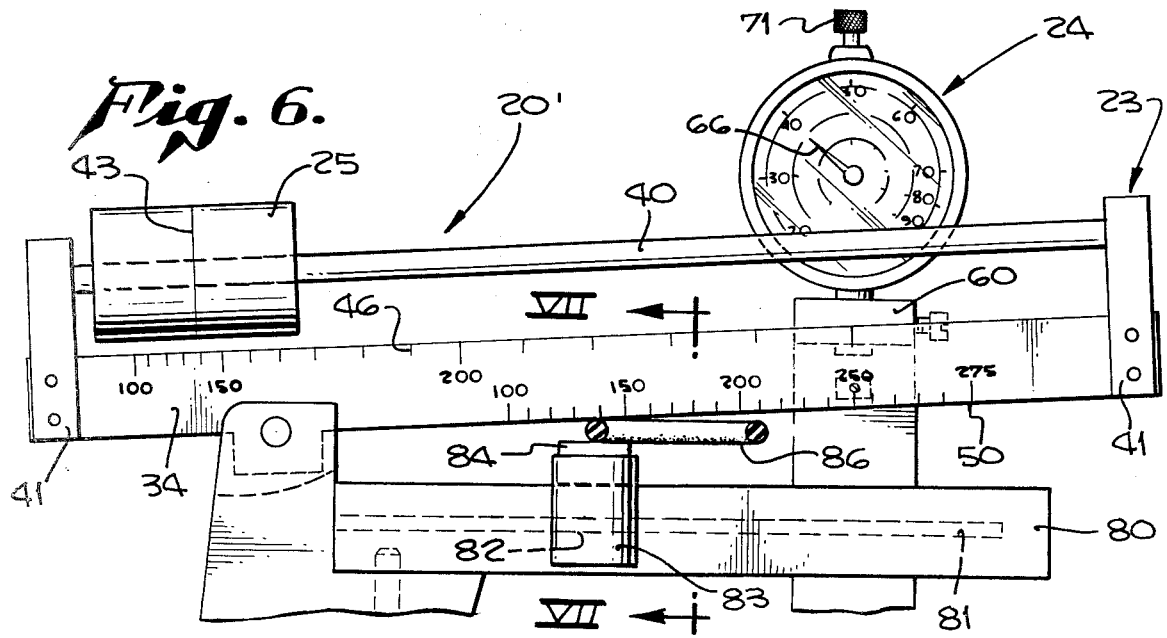

BEAM TYPE HARDNESS TESTER FOR ELASTOMERIC MATERIAL AND METHOD OF TESTING

BACKGROUND OF INVENTION

Hardness of a material is indicative of various physical qualities and characteristics of the material such as resilience, durability, uniformity, tensile strength, abrasion resistence, and other characteristics.

Prior methods of testing hardness of material include the Brinell hardness test in which a hardened ball is pressed into the sample material for a selected length of time and then the diameter of the indentation is measured and correlated to the amount of pressure used. The Rockwell hardness test is similar, but the depth of penetration of the ball is measured. Measurement of hardness of rubber like materials is on a Shore durometer scale which includes an "A" scale.

SUMMARY OF INVENTION

This invention particularly relates to the measurement of hardness of elastomeric material, a particular example being the hardness test of an O-ring of rubber or rubber like material. Other shapes or forms of elastomeric material may also be measured for hardness. The invention contemplates an apparatus and method for measuring hardness wherein hardness is directly read on the scale of a gauge without reference to charts, graphs, or making additional calculations.

The primary object of the present invention, therefore, is to provide a novel apparatus and method for measuring the hardness of elastomeric material.

An object of the invention is to provide an apparatus and method for testing hardness of elastomeric material in the form of an O-ring and rods of circular cross section.

Another object of the invention is to provide an apparatus and method for testing of elastomeric material in which the test is non-destructive of the material, accurately repetitive, and is simple to perform.

A more specific object of the present invention is to provide an apparatus in which a beam assembly with a weight thereon is cooperable with an anvil rod upon which is selectively positioned an O-ring of elastomeric material to be tested and wherein resulting deformation of the O-ring as it is gripped between the anvil rod and the beam assembly is directly read as Shore "A" scale hardness.

The invention particularly contemplates a novel method of measuring hardness of elastomeric material in which the diameter of the cross sectional dimension of the O-ring is measured, a selected compressive force determined by such measured diameter is imposed upon the sample, and the amount of deformation of the cross section of the sample is measured in novel manner.

Various other objects and advantages of the present invention will be readily apparent from the following description of the drawings in which exemplary embodiments of the invention are shown.

IN THE DRAWINGS

FIG. 1 is a side elevational view of an apparatus for testing hardness of elastomeric material embodying this invention.

FIG. 2 is a fragmentary elevational view, partly in section, illustrating hardness measurement of an O-ring having a cross sectional diameter of 0.200.

FIG. 3 is a transverse sectional view taken in the vertical plane indicated by line III—III of FIG. 2.

FIG. 4 is a fragmentary elevational view showing the right end of the beam assembly raised to check "set" position of the apparatus.

FIG. 5 is a vertical transverse sectional view taken in the vertical plane indicated by line V—V of FIG. 1.

FIG. 6 is a fragmentary side elevational view of a modification of the invention.

FIG. 7 is a fragmentary sectional view taken in the plane indicated by line VII—VII of FIG. 6.

Referring first to FIGS. 1-5 inclusive, an apparatus generally indicated at 20, embodying this invention is shown. Apparatus 20 generally comprises a base structure 21 which supports a horizontal fixed anvil member or rod 22. A beam assembly 23 pivotally mounted from base structure 21 extends over and along anvil member 22 and a suitable distance therebeyond. Gauge means 24 for measuring the vertical position of the beam assembly at the end of anvil member 22 is supported from the base of the structure 21 at one side of the beam assembly. Scale means are provided on the beam assembly for correlating the position of an O-ring sample to be tested and the position of a weight element 25 carried by the beam assembly as described in detail hereinafter.

Base structure 21 may comprise a rectangular base plate 30 of suitable thickness and weight. Adjacent one end of plate 30 an upstanding support block 31 is fixedly secured to plate 30 by recessed screw bolts 32. Support block 31 is provided at its top portion with an upwardly facing longitudinal groove and recess 33 which partially receives scale bar 34 of beam assembly 23 to limit lateral movement thereof. Recess and groove 33 provides a downwardly extended slot 35 having a downwardly curved bottom wall for accommodating a downwardly directed projection 36 on scale bar 34.

Beam assembly 23 is pivotally mounted from support block 31 by a pivot pin 37 carried in aligned openings 38 in the walls providing slot 35 in the support block, pin 37 extending through a portion of the downward projection 36 which provides sufficient metal section for carrying pin 37. Pivot pin 37 is suitably spaced from one end of the beam assembly 23. The axis of pin 37 lies in the plane of the bottom edge 50 of the scale bar 34.

Beam assembly 23 includes, in addition to scale bar 34, a beam member 40 positioned parallel to bar 34 and suitably secured in upstanding end members 41 fixed to ends of scale bar 34. Beam member 40 carries a weight element 25 which is slidably adjustably movable therealong. Weight element 25 is of selected weight and includes a set screw 42 to temporarily secure weight element 25 in a selected position on beam member 40. Weight element 25 utilizes a centrally located circumscribed line 43 as a reference indicia for properly positioning weight element 25 on beam member 40 for the testing of an O-ring sample of measured cross-sectional diameter.

Scale bar 34 may be of rectangular cross section and includes along its lower longitudinal edge portion, which extends to the right of support block 31, uniformly spaced scale indicia 45 representative of the dimension of the diameter of the cross section of an O-ring being tested. In this example scale indicia 45 represents dimensions of 0.100 to 0.275 inches.

The upper longitudinal edge portion of scale bar 34 includes scale indicia 46 also corresponding to the dimension of the diameter of the cross section of an O-ring being tested. Scale indicia 46 are not uniformly spaced, but are spaced in relation to the lever systems provided by the location of the axis of pivot pin 37 relative to the length and weight of the beam assembly 23 and the selected weight of element 25.

Anvil member 22 may be of selected diameter and fastened in the right end portion 47 of support block 31 by threading as at 48. Anvil member 22 may be of stainless steel and of precise cylindrical configuration. The uppermost linear element 49 of the cylindrical surface of anvil member 22 lies parallel to the longitudinal contact edge 50 of the scale bar 34 which normally rests in a horizontal position in groove 33.

Beam assembly 23 is provided with a laterally extending bar 54 secured by suitable countersunk screw means 55 to scale bar 34 approximately opposite the end of anvil member 22. Laterally extending bar 54 is provided with an upwardly facing insert 56 of magnetic material which coacts with tip 57 of sensing rod or armature 58 of gauge means 24 to provide a virtually forceless coupling of the beam assembly and gauge means.

Gauge means 24 provides a means for measuring the hardness of elastomeric material by sensing the vertical position of laterally extending bar 54 which is rigidly connected to the beam assembly 23 and thereby measures the vertical position of said beam assembly. The gauge means 24 may be supported at one side of the beam assembly by a suitable upstanding support member 60 secured to plate 30 by countersunk screw bolts 61. The upper end of support member 60 includes a vertical bore 62 through which stem 63 of gauge means 24 extends and is secured in selected vertical relationship therewith by a set screw 64.

Gauge means 24 is provided with a scale pointer or needle 66 associated with the sensing armature rod 58 in well-known manner. Gauge means 24 includes a plurality of concentrically arranged scales 67a, 67b, 67c having scale indicia representative of Shore "A" scale hardness.

Scales 67a, 67b, 67c are each correlated to normal or standard size cross sectional diameter of an O-ring sample to be tested. It will be understood that additional scales arranged in concentric manner may be added if desired for O-rings of other sizes.

The exemplary apparatus 20 may be designed for testing O-ring sizes having a cross sectional thickness of from 0.090 inches to 0.275 inches. Minimal inner diameter of the O-ring circle is about ⅜ inches which will permit an O-ring sample to be slidably positioned on anvil member 22 which in this example may have a diameter of 0.375 inches.

Before testing an O-ring sample, apparatus 20 must be calibrated. For this purpose, a 0.250 diameter calibration rod is positioned transversely of the anvil member 22 at the 0.250 position on the scale bar. The dial on the scale is moved to the set position indicated at 70, FIG. 4. An internal stop element, not shown, within gauge 24, limits vertical travel of sensing rod 58 at the point where the 0.250 inch diameter calibration rod just fits the space between the anvil bar 22 and the 0.250 inch position of the scale bar 34. The calibration rod is removed and the calibration is checked by raising the beam until it reaches the stop and the needle indicator returns to the set mark on the dial.

The method of testing the hardness of an O-ring with a calibrated apparatus 20 includes first accurately measuring the cross-sectional diameter of the O-ring to the closest 0.002 inches by use of calipers or a micrometer. The O-ring must not be deformed while making this measurement. If an examplary O-ring to be tested has a cross-sectional diameter of 0.210 for example, then the weight element 25 is moved so that reference line 43 which serves as a reference indicia is aligned with the scale mark 0.210 as shown in FIG. 2. Beam assembly 23 is then lifted upwardly about its pivot axis 37 until it reaches its upper stop position. The O-ring being tested is then slid over anvil member 49 until the axis of the O-ring cross section is directly opposite the scale mark 0.210 on the lower longitudinal edge of the scale bar. A slight resistance should be felt just as this position is reached. The beam assembly is then released and allowed to move pivotally downwardly to press the lower edge 50 of the scale bar against the upper surface of the O-ring. Deformation of the O-ring is measured by the change in position of the beam assembly and is indicated on the "A" scale reading in terms of hardness directly on the dial. The scale to be read on the dial is that scale which has indicia for O-rings of a cross-sectional diameter of 0.210.

It should be noted that the gauge means 24 maintains contact with the lateral extension 54 of the beam assembly by means of the magnetic insert 56. The use of a magnetic insert to maintain such contact eliminates the need for a spring restoring force usually provided in a gauge to move the sensing rod 58 to its normal position.

In the method of measuring the hardness of the O-ring, it will be apparent that an unstressed cross sectional dimension of the O-ring cross section is measured to determine the location of the O-ring on the anvil member and the location of the weight element 25 on the beam assembly. When the O-ring is properly positioned on the anvil member and the beam is lowered to rest edge 50 of the beam assembly on the O-ring, a predetermined amount of compression is imposed upon the O-ring sample; and this predetermined amount of compression is correlated to the unstressed thickness of the O-ring sample. Likewise the scale on the gauge means is specifically provided for standard sizes or thicknesses of O-rings so that the scale is at least closely accurate to the measured dimension of the O-ring sample. In the example of apparatus 20, the O-ring hardness is measured within ± two scale divisions on the "A" scale over a range of 20 to 90 on the "A" scale.

It may be noted that the "A" scale is extended over approximately 265 circular degrees; and therefore, provides a scale easy to read and a scale having a high degree of reading accuracy.

In the modification of the invention shown in FIGS. 6 and 7, the apparatus 20' is constructed and operable similar to the prior embodiment, the main difference between the two embodiments being in the manner in which the O-ring is carried by the anvil member. In this modification, anvil member 80 includes a rectangular cross section bar having a longitudinally extending keyway 81 for reception of a key 82 provided on a test support adaptor 83. Adaptor 83 is provided with a longitudinally extending ridge support element 84 having an ASTM "A" durometer indenter profile 85 directly opposed to edge 50 of the scale bar 34.

In this example of the invention, O-ring 86 is positioned at the selected location with respect to the scale bar 34 on the edge 85.

The procedure for testing hardness of an O-ring in horizontal position as shown in FIG. 6 is the same as in the prior embodiment; namely, the thickness of the O-ring 86 is measured, that thickness measurement determines the location of the weight element 25, in this example now positioned at 0.150 on the top scale of scale bar 34; and when the beam assembly is raised, the adaptor 83 is positioned generally beneath the scale mark 150 on the bottom of the scale bar, and the O-ring 86 is inserted between the knife-edge 85 and edge 50 so that its axis is immediately beneath the scale indicia 150. When the beam assembly 23 is lowered, the scale will read directly in "A" scale hardness.

It will be understood that various modifications and changes may be made in the apparatus and method described above which come within the spirit of the invention and all such changes and modifications coming within the scope of the appended claims are embraced thereby.

We claim:

1. An apparatus for testing hardness of elastomeric material of circular cross section, such as an O-ring, comprising, in combination:
   a base structure;
   a horizontal fixed anvil rod carried by said base structure;
   a beam assembly pivotally mounted on the base structure extending along and above said anvil rod and including
   a beam member and a selected weight element adjustably movable therealong,
   and a scale bar having two linear scales thereon and extending parallel to said beam member,
   said scale bar having a longitudinal edge cooperable with said anvil rod whereby said beam assembly is adapted to impart a compressive force on test material positioned between said scale bar edge and said anvil rod;
   and means for measuring the vertical position of said beam assembly when material being tested is positioned on said anvil rod at a location corresponding to the selected location of the weight element according to said scales on said scale bar.

2. An apparatus as stated in claim 1 wherein said two linear scales include indicia correlated to the thickness of the cross section of said material to be tested.

3. An apparatus as stated in claim 1 wherein one of the scales has indicia spaced uniformly according to change in cross sectional dimension of the material to be tested.

4. An apparatus as stated in claim 3 wherein the other scale has indicia spaced thereon according to the force moment of the weight element in relation to said pivotal mounting of the beam assembly.

5. An apparatus as stated in claim 1 wherein said measuring means is carried on said base structure at one side of the path of movement of said beam assembly.

6. An apparatus as stated in claim 5 wherein said scale bar includes
   a lateral extension adjacent to said measuring means;
   said measuring means including a vertical element having an end resting on said lateral extension.

7. An apparatus as stated in claim 6 wherein said lateral extension includes magnetic means for maintaining contact of said vertical element and lateral extension without transfer of force to said beam assembly.

8. An apparatus as stated in claim 1 wherein said measuring means includes
   a plurality of concentric scales, each scale being correlated with the cross sectional dimension of a material being tested.

9. In an apparatus as stated in claim 1 wherein said measuring means includes
   stop means for limiting maximum vertical excursion of said beam assembly during testing.

10. In an apparatus as stated in claim 1 including
    an anvil adaptor member slidably mounted on said anvil rod and having an edge for contact with material to be tested, whereby said material may be disposed horizontally when gripped between said edge and said beam assembly.

11. In an apparatus for testing hardness of an elastomeric material the combination of:
    fixed elongated anvil means;
    a beam assembly pivotally mounted relative to said anvil means and having an edge adapted to grip a test material positioned between said anvil means and beam assembly;
    a weight slidably movable on said beam assembly to a selected position;
    means for correlating the position of said weight on said beam assembly and the position of said material to be tested on said anvil means in accordance with a cross sectional dimension of said material to be tested;
    and means for measuring the change in position of the beam assembly when a material to be tested is positioned between said beam assembly and said anvil means at said selected position.

12. In a method of measuring hardness of an elastomeric sample having a measurable thickness, the steps of:
    measuring a selected cross sectional dimension of the sample;
    imposing on the sample a selected compressive force correlated to the measured cross sectional dimension;
    and measuring the deformation of the sample.

* * * * *